US012674186B2

(12) United States Patent
Creton

(10) Patent No.: US 12,674,186 B2
(45) Date of Patent: *Jul. 7, 2026

(54) EFFICIENT PRODUCT CLEAVAGE IN TEMPLATE-FREE ENZYMATIC SYNTHESIS OF POLYNUCLEOTIDES

(71) Applicant: DNA Script, Le Kremlin-Bicêtre (FR)

(72) Inventor: Sandrine Creton, Le Kremlin-Bicêtre (FR)

(73) Assignee: DNA SCRIPT SAS, Le Kremlin-Bicêtre (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/411,522

(22) Filed: Jan. 12, 2024

(65) Prior Publication Data

US 2025/0002958 A1     Jan. 2, 2025

Related U.S. Application Data

(63) Continuation of application No. 17/837,660, filed on Jun. 10, 2022, now Pat. No. 11,905,541, which is a continuation of application No. 16/981,595, filed as application No. PCT/EP2020/053417 on Feb. 11, 2020, now Pat. No. 11,359,221.

(30) Foreign Application Priority Data

Feb. 12, 2019   (EP) ..................................... 19305174

(51) Int. Cl.
*C12Q 1/68* (2018.01)
*C12P 19/14* (2006.01)
*C12P 19/34* (2006.01)

(52) U.S. Cl.
CPC .............. *C12P 19/14* (2013.01); *C12P 19/34* (2013.01)

(58) Field of Classification Search
CPC ........... C12P 19/34; C12P 19/38; C12P 19/14; C12Q 1/68; C12Q 1/6876; C12Q 1/6806; C12N 9/12; C12N 9/14
See application file for complete search history.

(56) References Cited

U.S. PATENT DOCUMENTS

| | | | |
|---|---|---|---|
| 4,772,691 | A | 9/1988 | Herman |
| 5,047,524 | A | 9/1991 | Andrus |
| 5,262,530 | A | 11/1993 | Andrus |
| 5,367,066 | A | 11/1994 | Urdea |
| 5,436,143 | A | 7/1995 | Hyman |
| 5,516,664 | A | 5/1996 | Hyman |
| 5,602,000 | A | 2/1997 | Hyman |
| 5,656,745 | A | 8/1997 | Bischofberger |
| 5,700,642 | A | 12/1997 | Monforte |
| 5,744,595 | A | 4/1998 | Srivastava |
| 5,763,594 | A | 6/1998 | Hiatt |
| 5,798,210 | A | 8/1998 | Canard |
| 5,808,045 | A | 9/1998 | Hiatt |
| 5,872,244 | A | 2/1999 | Hiatt |
| 5,917,031 | A | 6/1999 | Miura |
| 5,935,527 | A | 8/1999 | Andrus |
| 5,990,300 | A | 11/1999 | Hiatt |
| 6,214,987 | B1 | 4/2001 | Hiatt |
| 6,232,465 | B1 | 5/2001 | Hiatt |
| 6,623,929 | B1 | 9/2003 | Densham |
| 6,664,079 | B2 | 12/2003 | Ju |
| 6,777,189 | B2 | 8/2004 | Wei |
| 7,057,026 | B2 | 6/2006 | Barnes |
| 7,078,499 | B2 | 7/2006 | Odedra |
| 7,125,671 | B2 | 10/2006 | Sood |
| 7,270,951 | B1 | 9/2007 | Stemple |
| 7,345,159 | B2 | 3/2008 | Ju |
| 7,407,757 | B2 | 8/2008 | Brenner |
| 7,494,797 | B2 | 2/2009 | Mueller |
| 7,544,794 | B1 | 6/2009 | Benner |
| 7,566,537 | B2 | 7/2009 | Balasubramanian |
| 7,635,578 | B2 | 12/2009 | Ju |
| 7,713,698 | B2 | 5/2010 | Ju |
| 7,790,869 | B2 | 9/2010 | Balasubramanian |
| 7,932,025 | B2 | 4/2011 | Carr |
| 7,939,259 | B2 | 5/2011 | Kokoris |
| 8,034,923 | B1 | 10/2011 | Benner |
| 8,212,020 | B2 | 7/2012 | Benner |
| 8,263,335 | B2 | 9/2012 | Carr |
| 8,394,586 | B2 | 3/2013 | Balasubramanian |
| 8,674,086 | B2 | 3/2014 | Liu |
| 8,808,988 | B2 | 8/2014 | Zhao |

(Continued)

FOREIGN PATENT DOCUMENTS

| EP | 1165786 B1 | 7/2008 |
|---|---|---|
| EP | 2876166 B1 | 12/2016 |

(Continued)

OTHER PUBLICATIONS

Beabealashvilli et al, "Nucleoside 5'-triphosphates modified at sugar residues as substrates for calf thymus terminal deoxynucleotidyl transferase and for AMV reverse transcriptase," Biochim. Biophys. Acta., 868(2-3): 136-144 (1986).
Becker et al, "The enzymatic cleavage of phosphate termini from polynucleotides," J. Biol. Chem., 242(5): 936-950 (1967).
Cameron et al, "3'-phosphatase activity in T4 polynucleotide kinase," Biochemistry, 16(23): 5120-5126 (1977).
Canard et al, "DNA polymerase fluorescent substrates with reversible 3'-tags," Gene, 148: 1-6 (1994).
Canard et al, "Catalytic editing properties of DNA polymerases," Proc. Natl. Acad. Sci., 92: 10859-10863 (1995).
Chen et al, "The history and advances of reversible terminators used in new generations of sequencing technology," Genomics Proteomics Bioinformatics, 11: 34-40 (2013).
Delarue et al, "Crystal structures of a template-independent DNA polymerase: murine terminal deoxynucleotidyltransferase," EMBO J., 21(3): 427-439 (2002).

(Continued)

*Primary Examiner* — Maryam Monshipouri
(74) *Attorney, Agent, or Firm* — WCF IP

(57) ABSTRACT

The present invention is directed to methods and kits for template-free enzymatic synthesis of polynucleotides that include or enable a step of efficiently cleaving the polynucleotide products from its initiator using an endonuclease V activity and initiator with a 3'-penultimate deoxyinosine.

6 Claims, 1 Drawing Sheet

Specification includes a Sequence Listing.

(56)                 References Cited

U.S. PATENT DOCUMENTS

| | | | |
|---|---|---|---|
| 8,808,989 | B1 | 8/2014 | Efcavitch |
| 9,121,062 | B2 | 9/2015 | Balasubramanian |
| 9,388,463 | B2 | 7/2016 | Balasubramanian |
| 9,410,197 | B2 | 8/2016 | Bergmann |
| 9,896,709 | B2 | 2/2018 | Makarov |
| 9,957,549 | B2 | 5/2018 | Armour |
| 10,435,676 | B2 | 10/2019 | Champion |
| 10,752,887 | B2 | 8/2020 | Champion |
| 2011/0171649 | A1 | 7/2011 | Kutyavin |
| 2014/0363851 | A1 | 12/2014 | Efcavitch |
| 2014/0363852 | A1 | 12/2014 | Efcavitch |
| 2018/0016609 | A1 | 1/2018 | Chen |
| 2018/0023108 | A1 | 1/2018 | Chen |
| 2018/0201968 | A1 | 7/2018 | Chen |
| 2019/0144905 | A1 | 5/2019 | Chen |
| 2019/0264248 | A1 | 8/2019 | Ybert |
| 2019/0300923 | A1 | 10/2019 | Ybert |
| 2019/0338331 | A1 | 11/2019 | Chen |
| 2020/0002690 | A1 | 1/2020 | Ybert et al. |
| 2020/0231619 | A1 | 7/2020 | Ybert |
| 2021/0009994 | A1* | 1/2021 | Godron ................... C12N 15/10 |
| 2021/0254114 | A1 | 8/2021 | Creton |
| 2022/0356510 | A1* | 11/2022 | Godron ................ C12Q 1/6844 |

FOREIGN PATENT DOCUMENTS

| | | | |
|---|---|---|---|
| WO | WO1991/06678 | | 5/1991 |
| WO | WO1996/07669 | | 3/1996 |
| WO | WO2004/018497 | | 3/2004 |
| WO | WO2005/005667 | | 1/2005 |
| WO | WO2005/059096 | | 6/2005 |
| WO | WO2015/159023 | | 10/2015 |
| WO | WO2016/034807 | | 3/2016 |
| WO | 2017/216472 | A3 | 12/2017 |
| WO | WO2017/216472 | | 12/2017 |
| WO | 2018/134616 | A1 | 7/2018 |
| WO | WO2018/134616 | | 7/2018 |
| WO | WO2020/020608 | | 1/2020 |
| WO | WO2020/043846 | | 3/2020 |
| WO | 2020/077227 | A2 | 4/2020 |
| WO | WO2020/077227 | | 4/2020 |
| WO | WO2020/099451 | | 5/2020 |
| WO | WO2020/165137 | | 8/2020 |
| WO | WO2020/165334 | | 8/2020 |

OTHER PUBLICATIONS

Ferrero et al, "Chemoenzymatic transformations in nucleoside chemistry," Monatshefte fur Chemie, 131: 585-616 (2000).

Flickinger et al, "Differential incorporation of biotinylated nucleotides by terminal deoxynucleotidyl transferase," Nucleic Acids Research, 20(9): 2382 (1992).

Gates et al, "Endonuclease V of *Escherichia coli*," J. Biol. Chem., 252(5): 1647-1653 (1977).

Gebeyehu et al, "Novel biotinylated nucleotide—analogs for labeling and colorimetric detection of DNA," Nucleic Acids Research, 15(11): 4513-4534 (1987).

Grantham, "Amino acid difference formula to help explain protein evolution," Science, 185: 862-864 (1974).

Guo et al, "Four-color DNA sequencing with 3'-O-modified nucleotide reversible terminators and chemically cleavable fluorescent dideoxynucleotides," Proc. Natl. Acad. Sci., 105(27): 9145-9150 (2008).

Guo et al, "An integrated system for DNA sequencing by synthesis using novel nucleotide analogues," Acc. Chem. Res., 43(4): 551-563 (2010).

Huang et al, "Multiple cleavage activities of endonuclease V from Thermotoga maritima: recognition and strand nicking mechanism," Biochemistry, 40: 8738-8748 (2001).

Hutter et al, "Labeled nucleoside triphosphates with reversibly terminating aminoalkoxyl groups," Nucleosides, Nucleotides & Nucleic Acids, 29(11): 879-895 (2010).

Integrated DNA Technologies brochure, "Strategies for Attaching Oligonucleotides to Solid Supports," v.6 (2014).

IPR2013-00128 re U.S. Pat. No. 7,057,026 Final Written Decision (Jul. 25, 2013).

IPR2013-00266 re U.S. Pat. No. 8,158,346 Final Written Decision (Oct. 28, 2014).

IPR2017-02172 re U.S. Pat. No. 7,566,537 Decision (Apr. 20, 2018).

Jensen et al, "Template-independent enzymatic oligonucleotide synthesis (TiEOS): Its history, prospects, and challenges," Biochemistry, 57: 1821-1832 (2018).

Ju et al, "Four-color DNA sequencing by synthesis using cleavable fluorescent nucleotide reversible terminators," Proc. Natl. Acad. Sci., 103(52): 19635-19640 (2006).

Knapp et al, "Fluoride-Cleavable, Fluorescently Labelled Reversible Terminators: Synthesis and Use in Primer Extension," Chem. Eur. J., 17: 2903-2915 (2011).

Kobayashi et al, "A microfluidic device for conducting gas-liquid-solid hydrogenation reactions," Science, 304: 1305-1308 (2004).

Kore et al, "Synthesis and activity of modified cytidine 5'-monophosphate probes for T4 RNA ligase 1," Nucleosides Nucleotides Nucleic Acids, 28(4): 292-302 (2009).

Lee et al, "Endonuclease V-mediated deoxyinosine excision repair in vitro," DNA Repair, 9: 1073-1079 (2010).

Li et al, "A photocleavable fluorescent nucleotide for DNA sequencing and analysis," Proc. Natl. Acad. Sci., 100(2): 414-419 (2003).

Lin et al, "Recent patents and advances in the next-generation sequencing technologies," Recent Patents in Biomedical Engineering, 2008(1): 60-67 (2008).

Mathews et al, "Photo-cleavable nucleotides for primer free enzyme mediated DNA synthesis," Organic & Biomolecular Chemistry, 14: 8278 (2016).

Mi et al, "Dissecting endonuclease and exonuclease activities in endonuclease V from Thermotoga maritime," Nucleic Acids Research, 39(2): 536-544 (2011).

Michelson et al, "Characterization of the homopolymer tailing reaction catalyzed by terminal deoxynucleotidyl transferase," J. Biol. Chem., 257(24): 14773-14782 (1982).

Morse et al, "Detection of inosine in messenger RNA by inosine-specific cleavage," Biochemistry, 36(28): (Jul. 15, 1997).

Motea et al, "Terminal deoxynucleotidyl transferase: The story of a misguided DNA polymerase," Biochim Biophys Acta, 1804(5): 1151-1166 (2010).

Olejnik et al, "Photocleavable biotin derivatives: A versatile approach for the isolation of biomolecules," Proc. Natl. Acad. Sci., 92: 7590-7594 (1995).

Palla et al, "DNA sequencing by synthesis using 3'-O-azidomethyl nucleotide reversible terminators and surface-enhanced Raman spectroscopic detection," RCS Adv. 4: 49342 (2014).

Petrie et al, "A novel biotinylated adenylate analogue derived from pyrazolo[3,4-d] pyrimidine for labeling DNA probes," Bioconjug. Chem., 2(6): 441-446 (1991).

Rasolonjatovo et al, "Development of a new sequencing method: 3'-ester cleavage catalyzed by Taq DNA polymerase," Nucleosides & Nucleotides, 18(4&5): 1021-1022 (1999).

Schmitz et al, "Solid-phase enzymatic synthesis of oligonucleotides," Organic Lett., 1(11): 1729-1731 (1999).

Schott et al, "Single-step elongation of oligodeoxynucleotides using terminal deoxynucleotidyl transferase," Eur. J. Biochem., 143: 613-620 (1984).

Taunton-Rigby, "Oligonucleotide synthesis. III. Enzymatically removable acyl protecting groups," J. Org. Chem., 38(5): 977-985 (1973).

Ud-Dean, "A theoretical model for template-free synthesis of long DNA sequence," Syst. Synth. Biol., 2: 67-73 (2008).

Uemura et al., "Regioselective deprotection of 3', 5'-O-acylated pyrimidine nucleosides by lipase and esterase," Tetrahedron Lett., 30(29): 3819-3820 (1989).

Vik et al, "Endonuclease V cleaves at inosine in RNA," Nature Communications, 4: article No. 2271 (2013).

Wu et al, "3'-O-modified nucleotides as reversible terminators for pyrosequencing," Proc. Natl. Acad. Sci., 104(42): 16462-16467 (2007).

(56)                References Cited

OTHER PUBLICATIONS

Wu, Thesis, "Molecular engineering of novel nucleotide analogues for DNA sequencing by synthesis," Columbia University, 2008.

Yao et al, "Purification and characterization of a novel deoxyinosine-specific enzyme, deoxyinosine 3' endonuclease, from *Escherichia coli*," J. Biol. Chem., 269(23): 16260-16268 (1994).

Yao et al, "Interaction of deoxyinosine 3'-endonuclease from *Escherichia coli* with DNA containing deoxyinosine," J. Biol. Chem., 270 (48): 28609-28616 (1995).

Yao et al, "Further characterization of *Escherichia coli* Endonuclease V," J. Biol. Chem. 272(49): 30774-30779 (1997).

Zavgorodny et al, "1-Alkylthioalkylation of nucleoside hydroxyl functions and its synthetic applications: A new versatile method in nucleoside chemistry," Tetrahedron Lett., 32(51): 7593-7596 (1991).

Altschul et al., "Protein database searches using compositionally adjusted substitution matrices," FEBS Journal, 272: 5101-5109 (2005).

Altschul et al., "Gapped BLAST and PSI-BLAST: a new generation of protein database search programs," Nucleic Acids Research, 25(17): 3389-3402 (1997).

Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis," J. Org. Chem., 71: 3248-3252 (2006).

Needleman et al., "A general method applicable to the search for similarities in the amino acid sequence of two proteins," J. Mol. Biol., 48: 443-453 (1970).

Smith et al., "Identification of common molecular subsequences," J. Mol. Biol., 147:195-197 (1981).

International Search Report mailed May 29, 2020 for International Application No. PCT/EP2020/053417. (Submitted in related U.S. Appl. No. 16/981,595).

Written Opinion mailed May 29, 2020 for International Application No. PCT/EP2020/053417. (Submitted in related U.S. Appl. No. 16/981,595).

Vik, Erik Sebastian, et al. "Endonuclease V cleaves at inosines in RNA." Nature communications 4.1 (2013): 1-7. (Submitted in related U.S. Appl. No. 16/981,595).

* cited by examiner

SEQUENCE LISTING

```
Sequence total quantity: 15
SEQ ID NO: 1          moltype = AA  length = 510
FEATURE               Location/Qualifiers
REGION                1..510
                      note = TdT
source                1..510
                      mol_type = protein
                      organism = synthetic construct
SEQUENCE: 1
MDPLQAVHLG PRKKRPRQLG TPVASTPYDI RFRDLVLFIL EKKMGTTRRA FLMELARRKG  60
```

```
FRVENELSDS VTHIVAENNS GSDVLEWLQL QNIKASSELE LLDISWLIEC MGAGKPVEMM  120
GRHQLVVNRN SSPSPVPGSQ NVPAPAVKKI SQYACQRRTT LNNYNQLFTD ALDILAENDE  180
LRENEGSCLA FMRASSVLKS LPFPITSMKD TEGIPCLGDK VKSIIEGIIE DGESSEAKAV  240
LNDERYKSFK LFTSVFGVGL KTAEKWFRMG FRTLSKIQSD KSLRFTQMQK AGFLYYEDLV  300
SCVNRPEAEA VSMLVKEAVV TFLPDALVTM TGGFRRGKMT GHDVDFLITS PEATEDEEQQ  360
LLHKVTDFWK QQGLLLYCDI LESTFEKFKQ PSRKVDALDH FQKCFLILKL DHGRVHSEKS  420
GQQEGKGWKA IRVDLVMCPY DRRAFALLGW TGSRQFERDL RRYATHERKM MLDNHALYDR  480
TKRVFLEAES EEEIFAHLGL DYIEPWERNA                                    510

SEQ ID NO: 2              moltype = AA   length = 381
FEATURE                   Location/Qualifiers
REGION                    1..381
                          note = truncated mouse TdT
source                    1..381
                          mol_type = protein
                          organism = synthetic construct
SEQUENCE: 2
NSSPSPVPGS QNVPAPAVKK ISQYACQRRT TLNNYNQLFT DALDILAEND ELRENEGSCL   60
AFMRASSVLK SLPFPITSMK DTEGIPCLGD KVKSIIEGII EDGESSEAKA VLNDERYKSF  120
KLFTSVFGVG LKTAEKWFRM GFRTLSKIQS DKSLRFTQMQ KAGFLYYEDL VSCVNRPEAE  180
AVSMLVKEAV VTFLPDALVT MTGGFRRGKM TGHDVDFLIT SPEATEDEEQ QLLHKVTDFW  240
KQQGLLLYCD ILESTFEKFK QPSRKVDALD HFQKCFLILK LDHGRVHSEK SGQQEGKGWK  300
AIRVDLVMCP YDRRAFALLG WTGSRQFERD LRRYATHERK MMLDNHALYD RTKRVFLEAE  360
SEEEIFAHLG LDYIEPWERN A                                            381

SEQ ID NO: 3              moltype = AA   length = 380
FEATURE                   Location/Qualifiers
source                    1..380
                          mol_type = protein
                          organism = Bos taurus
SEQUENCE: 3
DYSATPNPGF QKTPPLAVKK ISQYACQRKT TLNNYNHIFT DAFEILAENS EFKENEVSYV   60
TFMRAASVLK SLPFTIISMK DTEGIPCLGD KVKCIIEEII EDGESSEVKA VLNDERYQSF  120
KLFTSVFGVG LKTSEKWFRM GFRSLSKIMS DKTLKFTKMQ KAGFLYYEDL VSCVTRAEAE  180
AVGVLVKEAV WAFLPDAFVT MTGGFRRGKK IGHDVDFLIT SPGSAEDEEQ LLPKVINLWE  240
KKGLLLYYDL VESTFEKFKL PSRQVDTLDH FQKCFLILKL HHQRVDSSKS NQQEGKTWKA  300
IRVDLVMCPY ENRAFALLGW TGSRQFERDI RRYATHERKM MLDNHALYDK TKRVFLKAES  360
EEEIFAHLGL DYIEPWERNA                                              380

SEQ ID NO: 4              moltype = AA   length = 380
FEATURE                   Location/Qualifiers
source                    1..380
                          mol_type = protein
                          organism = Bos taurus
SEQUENCE: 4
DYSDSTNPGP PKTPPIAVQK ISQYACQRRT TLNNCNQIFT DAFDILAENC EFRENEDSCV   60
TFMRAASVLK SLPFTIISMK DTEGIPCLGS KVKGIIEEII EDGESSEVKA VLNDERYQSF  120
KLFTSVFGVG LKTSEKWFRM GFRTLSKVRS DKSLKFTRMQ KAGFLYYEDL VSCVTRAEAE  180
AVSVLVKEAV WAFLPDAFVT MTGGFRRGKK MGHDVDFLIT SPGSTEDEEQ LLQKVMNLWE  240
KKGLLLYYDL VESTFEKLRL PSRKVDALDH FQKCFLIFKL PRQRVDSDQS SWQEGKTWKA  300
IRVDLVLCPY ERRAFALLGW TGSRQFERDL RRYATHERKM ILDNHALYDK TKRIFLKAES  360
EEEIFAHLGL DYIEPWERNA                                              380

SEQ ID NO: 5              moltype = AA   length = 376
FEATURE                   Location/Qualifiers
source                    1..376
                          mol_type = protein
                          organism = Bos taurus
SEQUENCE: 5
QYPTLKTPES EVSSFTASKV SQYSCQRKTT LNNCNKKFTD AFEIMAENYE FKENEIFCLE   60
FLRAASVLKS LPFPVTRMKD IQGLPCMGDR VRDVIEEIIE EGESSRAKDV LNDERYKSFK  120
EFTSVFGVGV KTSEKWFRMG LRTVEEVKAD KTLKLSKMQR AGFLYYEDLV SCVSKAEADA  180
VSSIVKNTVC TFLPDALVTI TGGFRRGKKI GHDIDFLITS PGQREDDELL HKGLLLYCDI  240
IESTFVKEQI PSRHVDAMDH FQKCFAILKL YQPRVDNSSY NMSKKCDMAE VKDWKAIRVD  300
LVITPFEQYA YALLGWTGSR QFGRDLRRYA THERKMMLDN HALYDKRKRV FLKAGSEEEI  360
FAHLGLDYVE PWERNA                                                  376

SEQ ID NO: 6              moltype = AA   length = 387
FEATURE                   Location/Qualifiers
source                    1..387
                          mol_type = protein
                          organism = Bos taurus
SEQUENCE: 6
SANPDPTAGT LNILPPTTKT ISQYACQRRT TINNHNQRFT DAFEILAKNY EFKENDDTCL   60
TFMRAISVLK CLPFEVVSLK DTEGLPWIGD EVKGIMEEII EDGESLEVQA VLNDERYQSF  120
KLFTSVFGVG LKTADKWYRM GFRTLNKIRS DKTLKLTKMQ KAGLCYYEDL IDCVSKAEAD  180
AVSLLVQDAV WTFLPDALVT ITGGFRRGKE FGHDVDFLIT SPGAEKEQED QLLQKVTNLW  240
KKQGLLLYCD LIESTFEDLK LPSRKIDALD HFQKCFLILK LYHHKEDKRK WEMPTGSNES  300
EAKSWKAIRV DLVVCPYDRY AFALLGWSGS RQFERDLRRY ATHEKKMMLD NHALYDKTKK  360
```

```
IFLKAKSEEE IFAHLGLEYI QPSERNA                                    387

SEQ ID NO: 7             moltype = AA   length = 381
FEATURE                  Location/Qualifiers
source                   1..381
                         mol_type = protein
                         organism = Bos taurus
SEQUENCE: 7
DCPASHDSSP QKTESAAVQK ISQYACQRRT TLNNHNHIFT DAFEILAENC EFRENEGSYV  60
TYMRAASVLK SLPFSIISMK DTEGIPCLAD KVKCVIEEII EDGESSEVKA VLNDERYKSF  120
KLFTSVFGVG LKTAEKWFRL GFRTLSGIMN DKTLKLTHMQ KAGFLYYEDL VSCVTRAEAE  180
AVGVLVKEAV WAFLPDAIVT MTGGFRRGKK VGHDVDFLIT SPEATEEQEQ QLLHKVITFW  240
EKEGLLLYCD LYESTFEKLK MPSRKVDALD HFQKCFLILK LHRECVDDGT SSQLQGKTWK  300
AIRVDLVVCP YECRAFALLG WTGSPQFERD LRRYATHERK MMLDNHALYD KTKRKFLSAD  360
SEEDIFAHLG LDYIEPWERN A                                          381

SEQ ID NO: 8             moltype = AA   length = 387
FEATURE                  Location/Qualifiers
source                   1..387
                         mol_type = protein
                         organism = Bos taurus
SEQUENCE: 8
EKYQLPEDED RSVTSDLDRD SISEYACQRR TTLKNYNQKF TDAFEILAEN YEFNENKGFC  60
TAFRRAASVL KCLPFTIVQV HDIEGVPWMG KQVKGIIEDI IEEGESSKVK AVLDNENYRS  120
VKLFTSVFGV GLKTSDKWYR MGLRTLEEVK RDKNLKLTRM QKAGFLHYDD LTSCVSKAEA  180
DAASLIVQDV VWKIVPNAIV TIAGGFRRGK QTGHDVDFLI TVPGSKQEEE ELLHTVIDIW  240
KKQELLLYYD LIESTFEDTK LPSRKVDALD HFQKCFAILK VHKEREDKGN SIRSKAFSEE  300
EIKDWKAIRV DLVVVPFEQY AFALLGWTGS TQFERDLRRY ATHEKKMMLD NHALYDKTKK  360
IFLNAASEEE IFAHLGLDYL EPWERNA                                    387

SEQ ID NO: 9             moltype = AA   length = 381
FEATURE                  Location/Qualifiers
source                   1..381
                         mol_type = protein
                         organism = Bos taurus
SEQUENCE: 9
DYTASPNPEL QKTLPVAVKK ISQYACQRRT TLNNYNNVFT DAFEVLAENY EFRENEVFSL  60
TFMRAASVLK SLPFTIISMK DTEGIPCLGD QVKCIIEEII EDGESSEVKA VLNDERYQSF  120
KLFTSVFGVG LKTSEKWFRM GFRTLSKIKS DKSLKFTPMQ KAGFLYYEDL VSCVTRAEAE  180
AVGVLVKEAV GAFLPDAFVT MTGGFRRGKK MGHDVDFLIT SPGSTDEDEE QLLPKVINLW  240
ERKGLLLYCD LVESTFEKLK LPSRKVDALD HFQKCFLILK LHHQRVDGGK CSQQEGKTWK  300
AIRVDLVMCP YERRAFALLG WTGSRQFERD LRRYASHERK MILDNHALYD KTKKIFLKAE  360
SEEEIFAHLG LDYIEPWERN A                                          381

SEQ ID NO: 10            moltype = AA   length = 382
FEATURE                  Location/Qualifiers
source                   1..382
                         mol_type = protein
                         organism = Bos taurus
SEQUENCE: 10
GDCPASHDSS PQKTESAAVQ KISQYACQRR TTLNNHNHIF TDAFEILAEN CEFRENEGSY  60
VTYMRAASVL KSLPFSIISM KDTEGIPCLA DKVKCVIEEI IEDGESSEVK AVLNDERYKS  120
FKLFTSVFGV GLKTAEKWFR LGFRTLSGIM NDKTLKLTHM QKAGFLYYED LVSCVTRAEA  180
EAVGVLVKEA VWAFLPDAIV TMTGGFRRGK KVGHDVDFLI TSPEATEEQE QQLLHKVITF  240
WEKEGLLLYC DLYESTFEKL KMPSRKVDAL DHFQKCFLIL KLHRECVDDG TSSQLQGKTW  300
KAIRVDLVVC PYECRAFALL GWTGSPQFER DLRRYATHER KMMLDNHALY DKTKRKFLSA  360
DSEEDIFAHL GLDYIEPWER NA                                         382

SEQ ID NO: 11            moltype = AA   length = 379
FEATURE                  Location/Qualifiers
source                   1..379
                         mol_type = protein
                         organism = Bos taurus
SEQUENCE: 11
EYSANPSPGP QATPAVYKIS QYACQRRTTL NNHNHIFTDA FEILAENYEF KENEGCYVTY  60
MRAASVLKSL PFTIVSMKDT EGIPCLEDKV KSIMEEIIEE GESSEVKAVL SDERYQCFKL  120
FTSVFGVGLK TSEKWFRMGF RSLSNIRLDK SLKFTQMQKA GFRYYEDIVS CVTRAEAEAV  180
DVLVNEAVRA FLPDAFITMT GGFRRGKKIG HDVDFLITSP ELTEEDEQQL LHKVMNLWEK  240
KGLLLYHDLV ESTFEKLKQP SRKVDALDHF QKCFLIFKLY HERVGGDRCR QPEGKDWKAI  300
RVDLVMCPYE CHAFALLGWT GSRQFERDLR RYASHERKMI LDNHALYDKT KRVFLQAENE  360
EEIFAHLGLD YIEPWERNA                                             379

SEQ ID NO: 12            moltype = AA   length = 384
FEATURE                  Location/Qualifiers
source                   1..384
                         mol_type = protein
                         organism = Bos taurus
SEQUENCE: 12
DASFGSNPGS QNTPPLAIKK ISQYACQRRT SLNNCNHIFT DALDILAENH EFRENEVSCV  60
```

-continued

```
AFMRAASVLK SLPFTIISMK DTKGIPCLGD KAKCVIEEII EDGESSEVKA ILNDERYQSF  120
KLFTSVFGVG LKTSEKWFRM GFRTLNKIMS DKTLKLTRMQ KAGFLYYEDL VSCVAKAEAD  180
AVSVLVQEAV WAFLPDAMVT MTGGFRRGKK LGHDVDFLIT SPGATEEEEQ QLLPKVINFW  240
ERKGLLLYHD LVESTFEKLK LPSRKVDALD HFQKCFLILK LHLQHVNGVG NSKTGQQEGK  300
NWKAIRVDLV MCPYERRAFA LLGWTGSRQF ERDLRRFATH ERKMMLDNHA LYDKTKRIFL  360
KAESEEEIFA HLGLDYIDPW ERNA                                         384

SEQ ID NO: 13            moltype = AA  length = 381
FEATURE                  Location/Qualifiers
source                   1..381
                         mol_type = protein
                         organism = Bos taurus
SEQUENCE: 13
DHSTSPSPGP QKTPALAVQK ISQYACQRRT TLNNCNRVFT DAFETLAENY EFRENEDSSV  60
IFLRAASVLR SLPFTITSMR DTEGLPCLGD KVKCVIEEII EDGESSEVNA VLNDERYKSF  120
KLFTSVFGVG LKTSEKWFRM GFRTLSRVRS DKSLHLTRMQ QAGFLYYEDL ASCVTRAEAE  180
AVGVLVKEAV GAFLPDALVT ITGGFRRGKK TGHDVDFLIT SPGSTEEKEE ELLQKVLNLW  240
EKKGLLLYYD LVESTFEKLK TPSRKVDALD HFPKCFLILK LHHQRVDGDK PSQQEGKSWK  300
AIRVDLVMCP YERHAFALLG WTGSRQFERD LRRYATHERK MMLDNHALYD KTKRVFLKAE  360
SEEDIFAHLG LDYIEPWERN A                                            381

SEQ ID NO: 14            moltype = AA  length = 394
FEATURE                  Location/Qualifiers
source                   1..394
                         mol_type = protein
                         organism = Bos taurus
SEQUENCE: 14
LTNSAPINCM TETPSLATKQ VSQYACERRT TLNNCNQKFT DAFEILAKDF EFRENEGICL  60
AFMRAISVLK CLPFTIVRMK DIEGVPWLGD QVKSIIEEII EDGESSSVKA VLNDERYRSF  120
QLFNSVFEVG LTDNGENGIA RGFQTLNEVI TDENISLTKT TLSTSLWNYL PGFLYYEDL   180
SCVAKEEADA VYLIVKEAVR AFLPEALVTL TGGFRRGKKI GHDVDFLISD PESGQDEQLL  240
PNIIKLWEKQ ELLLYYDLVE STFEKTKIPS RKVDAMDHFQ KCFLILKLHH QKVDSGRYKP  300
PPESKNHEAK NWKAIRVDLV MCPFEQYAYA LLGWTGSRQF ERDLRRYATH EKKMMLDNHA  360
LYDKTKKIFL KAESEEDIFT HLGLDYIEPW ERNA                              394

SEQ ID NO: 15            moltype = AA  length = 384
FEATURE                  Location/Qualifiers
source                   1..384
                         mol_type = protein
                         organism = Bos taurus
SEQUENCE: 15
SSELELLDVS WLIECMGAGK PVEMTGRHQL VKQTFCLPGF ILQDAFDILA ENCEFRENEA  60
SCVEFMRAAS VLKSLPFPII SVKDTEGIPW LGGKVKCVIE EIIEDGESSE VKALLNDERY  120
KSFKLFTSVF GVGLKTAERW FRMGFRTLST VKLDKSLTFT RMQKAGFLHY EDLVSCVTRA  180
EAEAVSVLVQ QAVVAFLPDA LVSMTGGFRR GKKIGHDVDF LITSPEATEE EEQQLLHKVT  240
NFWEQKGLLL YCDHVESTFE KCKLPSRKVD ALDHFQKCFL ILKLYRERVD SVKSSQQEGK  300
GWKAIRVDLV MCPYECRAFA LLGWTGSRQF ERDLRRYATH ERKMRLDNHA LYDKTKRVFL  360
KAESEEEIFA HLGLEYIEPL ERNA                                         384
```

EFFICIENT PRODUCT CLEAVAGE IN TEMPLATE-FREE ENZYMATIC SYNTHESIS OF POLYNUCLEOTIDES

RELATED APPLICATIONS

The present application is a continuation application of U.S. application Ser. No. 17/837,660, entitled "EFFICIENT PRODUCT CLEAVAGE IN TEMPLATE-FREE ENZYMATIC SYNTHESIS OF POLYNUCLEOTIDES," filed on Jun. 10, 2022, which is a continuation application of U.S. application Ser. No. 16/981,595 (now U.S. Pat. No. 11,359, 221), entitled "EFFICIENT PRODUCT CLEAVAGE IN TEMPLATE-FREE ENZYMATIC SYNTHESIS OF POLY-NUCLEOTIDES," filed on Sep. 16, 2020, which is a U.S. National Stage Entry of International Application No. PCT/EP2020/053417, entitled "EFFICIENT PRODUCT CLEAV-AGE IN TEMPLATE-FREE ENZYMATIC SYNTHESIS OF POLYNUCLEOTIDES," filed on Feb. 11, 2020, which claims priority to European Application No. 19305174.5 filed on Feb. 12, 2019. All above-identified applications are hereby incorporated by reference in their entireties.

INCORPORATION OF SEQUENCE LISTING

A computer readable form of the Sequence Listing is filed with this application by electronic submission and is incorporated into this application by reference in its entirety. The Sequence Listing is contained in the file created on Jan. 13, 2025, having the file name 2025-02-13_13500233US_seq-listing.xml, and is 20,451 bytes in size (as measured in the MS-Windows® operating system).

BACKGROUND

Interest in enzymatic approaches to polynucleotide synthesis has recently increased both because of increased demand for synthetic polynucleotides in many areas, such as synthetic biology, CRISPR-Cas9 applications, high-throughput sequencing, and the like, and because of the limitations of chemical approaches to polynucleotide synthesis, Jensen et al, Biochemistry, 57: 1821-1832 (2018). Currently, most enzymatic approaches employ a template-free polymerase to repeatedly add 3'-O-blocked nucleoside triphosphates to a single stranded initiator or an elongated strand attached to a support followed by deblocking until a polynucleotide of the desired sequence is obtained. Among the challenges of devising a practical implementation of such enzymatic synthesis is to find a cost-effective and efficient way to cleave a desired polynucleotide product from the initiator sequence and the support.

In view of the above, enzymatic synthesis of polynucle-otides would be advanced if methods were available for high efficiency cleavage of polynucleotide products from their single stranded initiators.

SUMMARY OF THE INVENTION

The present invention is directed to methods and kits for template-free enzymatic synthesis of polynucleotides that include or enable a step of efficiently cleaving the poly-nucleotide products from its initiator using an endonuclease V activity.

In one aspect, methods of the invention include a method of synthesizing polynucleotides of a predetermined sequence with the following steps: a) providing an initiator having a deoxyinosine penultimate to a 3'-terminal nucleotide having a free 3'-hydroxyl; b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed; and c) treating the polynucleotide with an endo-nuclease V activity to cleave the polynucleotide from the initiator.

The present invention advantageously overcomes the above problems in the field of enzymatic polynucleotide synthesis by providing an initiator having a deoxyinosine at the penultimate position from its 3' end. This permits effi-cient cleavage of the single stranded initiator at its terminal nucleotide releasing a polynucleotide product with a 5'-monophosphate.

DETAILED DESCRIPTION OF THE INVENTION

Figure 1:
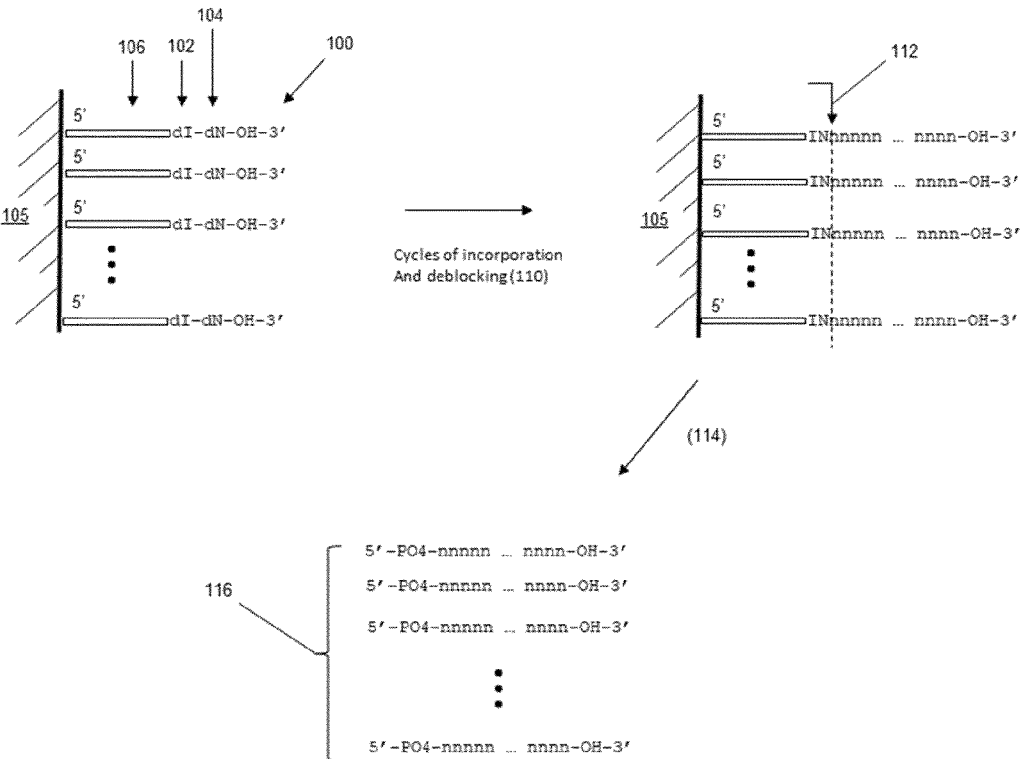
FIG. 1. illustrates an experimental set up for demonstrat-ing the cleavage efficiency of the present invention.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descrip-tions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edi-tion (Academic Press, 2008); and like references.

The present invention is based in part on a recognition and appreciation of the efficiency of using an endonuclease V activity and a deoxyinosine penultimate to the 3' terminal nucleotide of an initiator to cleave a polynucleotide product from an initiator, as compared to other cleavable nucleo-tides, such as deoxyuridine. In one aspect, it is believed that synthesis initiation by a terminal deoxynucleotidyl transferase (TdT) on an initiator with a penultimate deoxyinosine is much more efficient than initiation on other cleavable nucleotide configurations.

FIG. 1 provides a diagram of a template-free enzymatic synthesis method employing initiators with a penultimate deoxyinosine. Shown in this depiction are initiators (100) attached by their 5' ends to solid support (105). Each initiator (102) has a 3'-penultimate deoxyinosine (104) next to 3'-terminal nucleotide (106) that has a free 3' hydroxyl. After a predetermined number of cycles of enzymatic incorporation and de-blocking, a polynucleotide product is formed that is attached to solid support (105) by initiators (102). The polynucleotide product is cleaved from initiators (102) and support (105) by treating the attached product with an endonuclease V activity which recognizes the presence of the deoxyinosine and cleaves the strand on the 3' side (112) of terminal nucleotide (106) of the initiators. In some embodiments, the endonuclease V activity is provided by using a prokaryotic endonuclease V. In still other embodiments, the endonuclease V is an *E. coli* endonuclease V. As used herein, the term "endonuclease V activity" means an enzyme activity that catalyzes the following cleavage reaction in a single stranded DNA: 5' . . . NNINNNN . . . 3'→5' . . . NNIN+5'-PO$_4$—NNNN . . . 3' where N is any nucleotide and I is deoxyinosine. Cleavage (114) of polynucleotides (116) by an endonuclease V activity leaves a 5'-monophosphate on the polynucleotides, which optionally may be removed by a step of treating them with a 5'-phosphatase.

Enzymes with endonuclease V activity are available from commercial enzyme suppliers, for example, New England Biolabs (Beverly, MA, USA), NzyTech (Lisbon, Portugal). Such enzymes may be used with the supplier's recommended cleavage buffers (e.g. 50 mM K—Ac, 20 mM Tris-Ac, 10 mM Mg—Ac, 1 mM DTT at pH 7.9). Typical cleavage conditions are as follows: 70 U of Endo V in 50 µl of Nzytech buffer at 37° C. for 500 pmol synthesis scale on resin. Typical cleavage times are from 5 to 60 minutes, or from 10 to 30 minutes. Optionally, endonuclease activity of the above enzymes may be heat inactivated by incubation at 65° C. or higher for 20 minutes. Optionally, the Nzytech endonuclease V comprises a His tag that allows convenient removal of the enzyme from reaction mixtures in preparation of final products.

Template-Free Enzymatic Synthesis

Template-free enzymatic synthesis of polynucleotides may be carried out by a variety of known protocols using template-free polymerases, such as terminal deoxynucleotidyl transferase (TdT), including variants thereof engineered to accommodate more efficiently 3'-O-blocked deoxynucleoside triphosphates (3'-O-blocked dNTPs), e.g. Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57:1821-1832 (2018); Mathews et al, Organic & Biomolecular Chemistry, DOI: 0.1039/c6ob01371f (2016); Schmitz et al, Organic Lett., 1(11): 1729-1731 (1999).

In some embodiments, an ordered sequence of nucleotides is coupled to an initiator nucleic acid using a TdT in the presence of 3'-O-reversibly blocked dNTPs in each synthesis step. In some embodiments, the method of synthesizing an oligonucleotide comprises the steps of (a) providing an initiator having a free 3'-hydroxyl; (b) reacting under extension conditions an initiator or an extension intermediate having a free 3'-hydroxyl with a TdT in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized. (Sometime "an extension intermediate" is also referred to as an "elongation fragment.") In some embodiments, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

The above method may also include capping step(s) as well as washing steps after the reacting, or extending, step, as well as after the deblocking step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments that comprise serial synthesis of oligonucleotides, capping steps may be undesirable as capping may prevent the production of equal molar amounts of a plurality of oligonucleotides. Without capping, sequences will have a uniform distribution of deletion errors, but each of a plurality of oligonucleotides will be present in equal molar amounts. This would not be the case where non-extended fragments are capped.

In some embodiments, reaction conditions for an extension or elongation step may comprising the following: 2.0 µM purified TdT; 125-600 µM 3'-O-blocked dNTP (e.g. 3'-O—NH$_2$-blocked dNTP); about 10 to about 500 mM potassium cacodylate buffer (pH between 6.5 and 7.5) and from about 0.01 to about 10 mM of a divalent cation (e.g. CoCl$_2$ or MnCl$_2$), where the elongation reaction may be carried out in a 50 µL reaction volume, at a temperature within the range RT to 45° C., for 3 minutes. In embodiments, in which the 3'-O-blocked dNTPs are 3'-O—NH$_2$-blocked dNTPs, reaction conditions for a deblocking step may comprise the following: 700 mM NaNO$_2$; 1 M sodium acetate (adjusted with acetic acid to pH in the range of 4.8-6.5), where the deblocking reaction may be carried out in a 50 µL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: U.S. Pat. Nos. 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl) phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments, such as those described above. It is understood that other blocking group pairs, or groups containing more than two, may be available for use in these embodiments of the invention.

| | |
|---|---|
| 3'-O—NH2 | 3'-O-azidomethyl |
| 3'-O—NH2 | 3'-O-allyl |
| 3'-O—NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM MgCl₂, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoester/nucleotidyl-2',3'-cyclic phosphate, nucleotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte fur Chemie, 131:585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

As used herein, an "initiator" (or equivalent terms, such as, "initiating fragment," "initiator nucleic acid," "initiator oligonucleotide," or the like) refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In one embodiment, the initiating fragment possesses between 3 and 100 nucleotides, in particular between 3 and 20 nucleotides. In one embodiment, the initiating fragment is single-stranded. In an alternative embodiment, the initiating fragment is double-stranded. In a particular embodiment, an initiator oligonucleotide synthesized with a 5'-primary amine may be covalently linked to magnetic beads using the manufacturer's protocol. Likewise, an initiator oligonucleotide synthesized with a 3'-primary amine may be covalently linked to magnetic beads using the manufacturer's protocol. A variety of other attachment chemistries amenable for use with embodiments of the invention are well-known in the art, e.g. Integrated DNA Technologies brochure, "Strategies for Attaching Oligonucleotides to Solid Supports," v.6 (2014); Hermanson, Bioconjugate Techniques, Second Edition (Academic Press, 2008); and like references.

Many of the 3'-O-blocked dNTPs employed in the invention may be purchased from commercial vendors or synthesized using published techniques, e.g. U.S. Pat. No. 7,057, 026; International patent publications WO2004/005667, WO91/06678; Canard et al, Gene (cited above); Metzker et al, Nucleic Acids Research, 22: 4259-4267 (1994); Meng et al, J. Org. Chem., 14: 3248-3252 (3006); U.S. patent publication 2005/037991. In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

$$—O—Z$$

wherein —Z is any of —C(R')₂—O—R", —C(R')₂—N(R")₂, —C(R')₂—N(H)R", —C(R')₂—S—R" and —C(R')₂—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')₂ represents a group of formula =C(R''')₂ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')₂—F, the F is exchanged for OH, SH or NH₂, preferably OH, which intermediate dissociates under aqueous conditions to afford a molecule with a free 3'-OH; with the proviso that where Z is —C(R')₂—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA).

In a further particular embodiment, the 3'-blocked nucleotide triphosphate is blocked by either a 3'-O-azidomethyl, 3'-O—NH$_2$ or 3'-O-allyl group.

In still other embodiments, 3'-O-blocking groups of the invention include 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), and 3'-O-propargyl.

In some embodiments, 3'-O-protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

In some embodiments, enzymatic synthesis methods employ TdT variants that display increased incorporation activity with respect to 3'-O-modified nucleoside triphosphates. For example, such TdT variants may be produced using techniques described in Champion et al, U.S. Pat. No. 10,435,676, which is incorporated herein by reference. In some embodiments, a TdT variant is employed having an amino acid sequence at least 60 percent identical to SEQ ID NO: 2 and a substitution at a first arginine at position 207 and a substitution at a second arginine at position 325, or functionally equivalent residues thereof. In some embodiments, a terminal deoxynucleotidyl transferase (TdT) variant is employed that has an amino acid sequence at least sixty percent identical to an amino acid sequence selected from SEQ ID NO: 2, 3, 4, 5, 6, 7, 8, 9, 10, 11, 12, 13, 14 or 15 with a substitution of arginine ("first arginine") at position 207 with respect to SEQ ID NOs 2, 3, 4, 6, 7, 9, 12 and 13, at position 206 with respect to SEQ ID NO 5, at position 208 with respect to SEQ ID NOs 8 and 10, at position 205 with respect to SEQ ID NO 11, at position 216 with respect to SEQ ID NO 14 and at position 210 with respect to SEQ ID NO 15; and a substitution of arginine ("second arginine") at position 325 with respect to SEQ ID NOs 2, 9 and 13, at position 324 with respect to SEQ ID NOs 3 and 4, at position 320 with respect to SEQ ID NO 5, at position 331 with respect to SEQ ID NOs 6 and 8, at position 323 with respect to SEQ ID NO 11, at position 328 with respect to SEQ ID NOs 12 and 15, and at position 338 with respect to SEQ ID NO 14; or functionally equivalent residues thereof; wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100.

In regard to (ii), such 3'-O-modified nucleotide may comprise a 3'-O—NH$_2$-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, TdT variants used in the invention have substitutions as shown in Table 1 or functionally equivalent residue positions in other TdTs.

TABLE 1

| SEQ ID NO | Substitutions | | | | |
|---|---|---|---|---|---|
| 1 | M192R/Q | C302G/R | R336L/N | R454P/ N/A/V | E457N/ L/T/S/K |
| 2 | M63R/Q | C173G/R | R207L/N | R325P/ N/A/V | E328N/ L/T/S/K |
| 3 | M63R/Q | C173G/R | R207L/N | R324P/ N/A/V | E327N/ L/T/S/K |
| 4 | M63R/Q | C173G/R | R207L/N | R324P/ N/A/V | E327N/ L/T/S/K |
| 5 | — | C172G/R | R206L/N | R320P/ N/A/V | — |

TABLE 1-continued

| SEQ ID NO | | | Substitutions | | |
|---|---|---|---|---|---|
| 6 | M63R/Q | C173G/R | R207L/N | R331P/ N/A/V | E334N/ L/T/S/K |
| 7 | M63R/Q | C173G/R | R207L/N | — | E328N/ L/T/S/K |
| 8 | — | C174G/R | R208L/N | R331P/ N/A/V | E334N/ L/T/S/K |
| 9 | M73R/Q | C173G/R | R207L/N | R325P/ N/A/V | E328N/ L/T/S/K |
| 10 | M64R/Q | C174G/R | R208L/N | — | E329N/ L/T/S/K |
| 11 | M61R/Q | C171G/R | R205L/N | R323P/ N/A/V | E326N/ L/T/S/K |
| 12 | M63R/Q | C173G/R | R207L/N | R328P/ N/A/V | E331N/ L/T/S/K |
| 13 | — | C173G/R | R207L/N | R325P/ N/A/V | E328N/ L/T/S/K |
| 14 | M63R/Q | C182G/R | R216L/N | R338P/ N/A/V | E341N/ L/T/S/K |
| 15 | M66R/Q | C176G/R | R210L/N | R328P/ N/A/V | E331N/ L/T/S/K |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 2A.

TABLE 2A

| Synonymous Sets of Amino Acids I | |
|---|---|
| Amino Acid | Synonymous Set |
| Ser | Ser, Thr, Gly, Asn |
| Arg | Arg, Gln, Lys, Glu, His |
| Leu | He, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, He |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 2B.

TABLE 2B

| Synonymous Sets of Amino Acids II | |
|---|---|
| Amino Acid | Synonymous Set |
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Kits

The invention includes kits for carrying out methods of the invention. In some embodiments, a kit of the invention comprises an initiator attached to a support by a 5' end and having a deoxyinosine penultimate to a 3' end and free 3'-hydroxyl. In some embodiments, a kit of the invention further includes an endonuclease V capable of cleaving an initiator-polynucleotide conjugate 3' of a terminal nucleotide of the initiator. In some such kits, the endonuclease V has a capture moiety to permit removal from a reaction mixture. In some kits, such capture moiety is a His tag. In some embodiments, initiators of a kit have a 3'-10 terminal sequence of 5'-dI-dT-3'. In some embodiments, initiators of a kit have a 3'-terminal sequence of 5'-dI-dG-3'. In some embodiments, initiators of a kit have a 3'-terminal sequence of 5'-dI-dA-3'. In some embodiments, initiators of a kit have a 3'-terminal sequence of 5'-dI-dT-3', 5'-dI-dG-3', or 5'-dI-dA-3'. In some embodiments, such support is a solid support. Such solid support may comprise beads, such as magnetic bead, a planar solid, such as a glass slide, or a membrane, or the like. In some embodiments, a kit of the invention may further include a template-free polymerase and 3'-O-blocked nucleoside triphosphates of one or more of deoxyadenosine, deoxyguanosine, thymidine, deoxyuridine and deoxycytidine. In some kits, such template-free polymerase may be a TdT. In some embodiments, such TdT may be a TdT variant described herein. In some embodiments, a kit of the invention may further include a de-blocking agent which is capable of removing 3' blocking groups from incorporated 3'-O-blocked nucleotides.

Example

In this example, the efficiency of using deoxyinosine/endo V cleavage is compared to deoxyuridine/USER cleavage and the effects on cleavage of nucleotides adjacent to dI are assessed. 5'-amino-poly(dT) oligonucleotides containing dI were coupled to carboxyl groups of magnetic beads using EDC in a conventional reaction. In all experiments, initiators comprised either (1) a 5'-10mer polyT segment followed by a deoxyinosine and 3' terminal dT, or (2) a 5'-10mer polyT segment followed by a terminal deoxyuridine. In some experiments, initiators were extended by a 20mer polyT segment followed by a final dA labeled with a Cy5 dye, all using a TdT enzyme and 3'-O—NH₂-blocked nucleoside triphosphates (except for the labeled terminal dA). In other experiments, the initiators were extended by the indicated dinucleotide sequences followed by a 18mer poly(dT) and a final dA labeled with a Cy5 dye, all using a TdT enzyme and 3'-O—NH₂-blocked nucleoside triphosphates (except for the labeled terminal dA). After cleavage as indicated (USER or Endo V), the cleaved labeled polynucleotides were analyzed by polyacrylamide gel electrophoresis.

Figure 2:
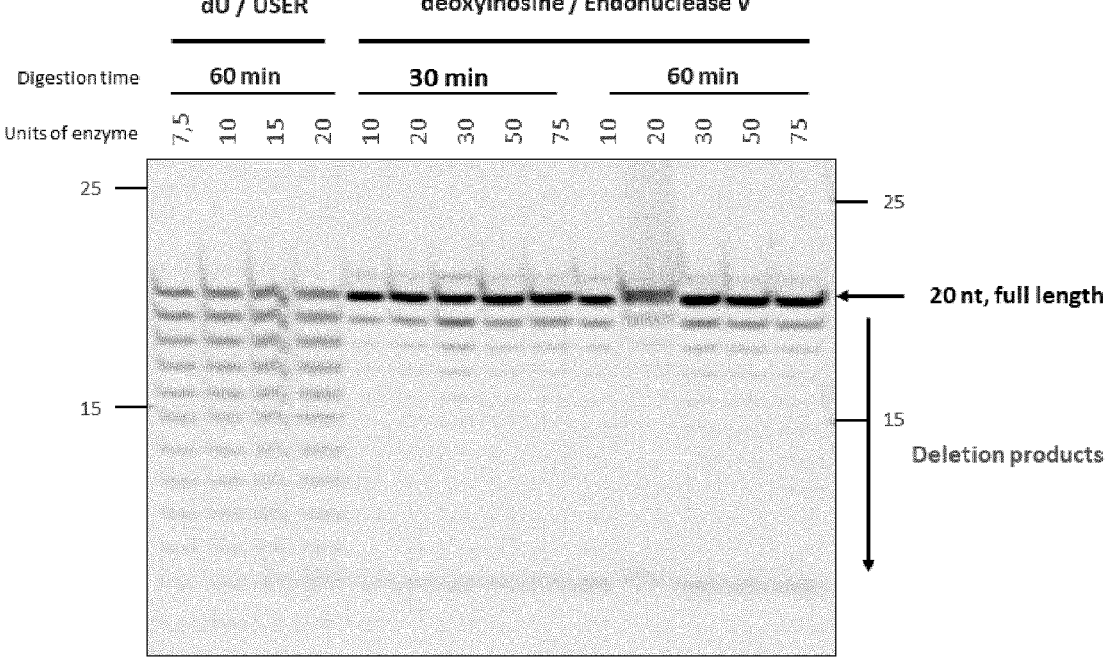
FIG. 2 shows data comparing efficiencies of USER/deoxyuridine cleavage and Endo V/inosine cleavage.

FIG. 2 shows electrophoresis data comparing synthesis products of initiators having terminal deoxyuridines with synthesis products of initiators having penultimate deoxyinosines. The bands in the four ladders on the left of the gel corresponding to deoxyuridine initiators show failure sequences that are significantly more intense than the corresponding bands from deoxyinosine initiators in the right-most 10 ladders indicating that initiators with penultimate deoxyinosines result in more efficient synthesis than initiators with terminal deoxyuridines.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

"Functionally equivalent" in reference to amino acid positions in two or more different TdTs means (i) the amino acids at the respective positions play the same functional role in an activity of the TdTs, and (ii) the amino acids occur at homologous amino acid positions in the amino acid sequences of the respective TdTs. It is possible to identify positionally equivalent or homologous amino acid residues in the amino acid sequences of two or more different TdTs on the basis of sequence alignment and/or molecular modelling. In some embodiments, functionally equivalent amino acid positions belong to sequence motifs that are conserved among the amino acid sequences of TdTs of evolutionarily related species, e.g. genus, families, or the like. Examples of such conserved sequence motifs are described in Motea et al, Biochim. Biophys. Acta. 1804(5): 1151-1166 (2010); Delarue et al, EMBO J., 21: 427-439 (2002); and like references.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., fluorescent labels, such as mutually quenching fluorescent labels, fluorescent label linking agents, enzymes, quenching agents, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels and/or quenching agents.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/ or ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr). In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A kit for enzymatically synthesizing a polynucleotide comprising an initiator attached to a support by a 5' end and having a 3'-penultimate deoxyinosine and a 3'-terminal nucleotide having a free 3'-hydroxyl.

2. The kit of claim 1, wherein said support is a solid support.

3. The kit of claim 1, wherein the solid support is selected from the group consisting of a magnetic bead, a planar solid, and a membrane.

4. The kit of claim 1, further comprising a de-blocking agent.

5. The kit of claim 1, wherein the initiator is in a container.

6. The kit of claim 3, wherein the planar solid is a glass slide.

* * * * *